United States Patent [19]

Uno et al.

[11] 4,256,753
[45] Mar. 17, 1981

[54] 4-(2-PYRIDYLAMINO)PHENYLACETIC ACID DERIVATIVES

[75] Inventors: Hitoshi Uno, Takatsuki; Yasutaka Nagai, Muko; Katsuhiko Hino, Izumisano; Hideo Nakamura, Tenri, all of Japan

[73] Assignee: Dainippon Pharmaceutical Co., Ltd., Osaka, Japan

[21] Appl. No.: 95,572

[22] Filed: Nov. 19, 1979

[30] Foreign Application Priority Data

Nov. 27, 1978 [JP] Japan .................. 53/146952

[51] Int. Cl.³ .................. C07D 213/74; A61K 31/44
[52] U.S. Cl. .................. 424/263; 546/312; 546/307
[58] Field of Search .......... 546/304, 307, 312; 424/263

[56] References Cited

U.S. PATENT DOCUMENTS 3,766,260 10/1973 Carney et al. .............. 562/441
3,957,850 5/1976 Bouchara .................. 560/19

FOREIGN PATENT DOCUMENTS 50-149668 11/1975 Japan .................. 546/304

*Primary Examiner*—Henry R. Jiles
*Assistant Examiner*—Jane T. Fan
*Attorney, Agent, or Firm*—Stevens, Davis, Miller & Mosher

[57] ABSTRACT

Novel 4-(2'-pyridylamino)phenylacetic acid derivatives of the formula:

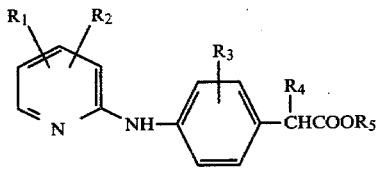

wherein $R_1$ is hydrogen, a halogen, a lower alkyl having 1 to 3 carbon atoms, or nitro, $R_2$ is hydrogen, a halogen, or a lower alkyl having 1 to 3 carbon atoms, $R_3$ is hydrogen, a halogen, or a lower alkyl having 1 to 3 carbon atoms, $R_4$ is hydrogen or a lower alkyl having 1 to 3 carbon atoms, $R_5$ is hydrogen or $-CH_2CH_2OR_6$ wherein $R_6$ is a lower alkyl having 2 or 3 carbon atoms and being substituted with 1 or 2 hydroxy groups, provided that $R_1$ or $R_2$ is not 4-halogen, or pharmaceutically acceptable salts thereof, and a process for the preparation thereof, pharmaceutical composition of said compounds, and a method of using said compounds as anti-inflammatory and analgesic agents. They have excellent anti-inflammatory and analgesic activities with an extremely weak ulcerogenicity in the gastrointestinal tract. Some of the compounds have superior inhibitory activity against chronic inflammation mediated by cellular immunity.

9 Claims, No Drawings

4-(2-PYRIDYLAMINO)PHENYLACETIC ACID DERIVATIVES

The present invention relates to novel 4-(2'-pyridylamino)phenylacetic acid derivatives having anti-inflammatory and analgesic activities, a process for the preparation thereof, a method of using the same and compositions thereof.

It is disclosed in U.S. Pat. No. 3,766,260 that the compounds of the formula (II)

in which $R_1'$ is hydrogen or lower alkyl, $R_2'$ is hydrogen, lower alkyl, alkenyl, cycloalkyl, cycloalkenyl, cycloalkyl-alkyl or cycloalkenyl-alkyl, Ph is a 1,3- or 1,4-phenylene radical, $R_3'$ is lower alkyl, alkenyl, hydroxyalkyl, alkoxyalkyl, aminoalkyl, cycloalkyl, cycloalkenyl, cycloalkyl-alkyl or cycloalkenyl-alkyl, wherein hetero-atoms are separated from the nitrogen atom by at least 2 carbon atoms, and $R_4'$ is an aryl radical, are useful as an anti-inflammatory agent. It is disclosed in this U.S. patent, column 2, lines 59–62 that the aryl radical $R_4'$ is preferably a monocyclic iso- or hetero-cyclic aryl radical, such as an unsubstituted or substituted phenyl, pyridyl, furyl or thiophenyl radical wherein the substituents are those shown above for Ph. However, there is not specifically disclosed the compound of the formula (II) wherein $R_4'$ is an unsubstituted or substituted pyridyl radical.

Besides, it is disclosed in Japanese Patent Publication (unexamined) No. 149,668/1975 that the compounds of the formula (III)

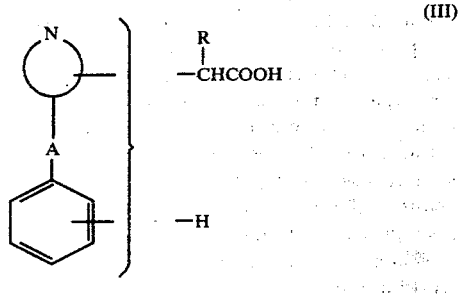

wherein

is pyridyl, pyrimidinyl, imidazolyl, tetrazolyl or thiazolyl, R is a hydrocarbon group, A is oxygen, sulfur, imino, or a hydrocarbon group-substituted imino group, said

and benzene ring in the formula (III) may have 1 to 3 substituents which do not affect the reaction, or may have a fused benzene ring or fused alicyclic ring, and the group

may be located on the fused benzene ring, provided that when

is not thiazolyl, A is oxygen or sulfur, have an excellent anti-inflammatory and analgesic activities.

It is known that anti-inflammatory and analgesic agents have usually an undesirable side effect of ulcerogenicity in the gastrointestinal tract. The present inventors have intensively studied to find a new compound which has excellent anti-inflammatory and analgesic activities but has a weak or little ulcerogenicity in the gastrointestinal tract. As a result, it has been found that the desired compound can be obtained by replacing one hydrogen atom of amino group of p-aminophenylacetic acid derivatives with 2-pyridyl group.

An object of the present invention is to provide novel 4-(2'-pyridylamino)phenylacetic acid derivatives which have excellent anti-inflammatory and analgesic activities with weak ulcerogenicity in the gastrointestinal tract. Another object of the invention is to provide a process for the preparation of said compounds. A further object of the invention is to provide a use of the compounds as anti-inflammatory and analgesic agents. A still further object of the invention is to provide a composition of the active compound. These and other objects and advantages of the present invention will be apparent to persons skilled in the art from the following description.

The compounds of the present invention are represented by the following formula (I):

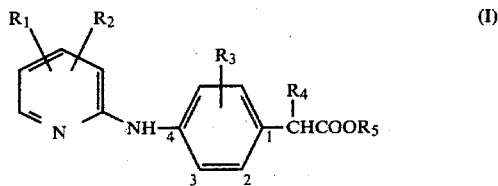

wherein $R_1$ is hydrogen, a halogen, a lower alkyl having 1 to 3 carbon atoms, or nitro, $R_2$ is hydrogen, a halogen, or a lower alkyl having 1 to 3 carbon atoms, $R_3$ is hydrogen, a halogen, or a lower alkyl having 1 to 3 carbon atoms, $R_4$ is hydrogen or a lower alkyl having 1 to 3 carbon atoms, $R_5$ is hydrogen or $-CH_2CH_2OR_6$ wherein $R_6$ is a lower alkyl having 2 or 3 carbon atoms and being substituted with 1 or 2 hydroxy groups, provided that $R_1$ or $R_2$ is not 4-halogen.

The compounds of the present invention include also a pharmaceutically acceptable salt thereof. The pharmaceutically acceptable salt denotes salts of the compounds of the formula (I) wherein $R_5$ is hydrogen with inorganic or organic bases. The salts with inorganic bases include sodium, potassium, calcium, magnesium, aluminum and ammonium salts. The salts with organic bases include salts with isopropylamine, diethylamine, ethanolamine, piperidine, tromethamine, lysine, or the like.

The compounds of the formula (I) wherein $R_4$ is a lower alkyl contain an asymmetric carbon, and hence, there are racemic compounds and optical isomers. The present invention includes also these racemic compounds and optical isomers.

In the formula (I), the halogen denotes fluorine, chlorine and bromine atoms. The lower alkyl denotes methyl, ethyl, propyl and isopropyl, preferably methyl. The group —$CH_2CH_2OR_6$ includes preferably 2-(2-hydroxyethoxy)ethyl, 2-(2,3-dihydroxypropoxy)ethyl, or the like.

The compounds of the formula (I) and a pharmaceutically acceptable salt thereof have excellent anti-inflammatory and analgesic activities with a weak ulcerogenicity in the gastrointestinal tract and hence have a very large safety margin. Some of the compounds of the present invention have an inhibitory activity against chronic inflammation mediated by cellular immunity and also an anti-allergic activity with an extremely weak ulcerogenicity in the gastrointestinal tract.

Preferred compounds of the present invention are the compounds of the formula (I) wherein $R_1$ is hydrogen, a halogen or nitro, and $R_2$ is hydrogen or a halogen. More preferred compounds are the compounds of the formula (I) wherein $R_1$ and $R_2$ are both hydrogen, $R_3$ is hydrogen, 3-halogen or 3-methyl, $R_4$ is methyl, and $R_5$ is hydrogen or 2-(2-hydroxyethoxy)ethyl. Particularly suitable compounds are as follows:

2-[4-(2'-pyridylamino)phenyl]propionic acid,
2-[3-chloro-4-(2'-pyridylamino)phenyl]propionic acid, and
2-[3-methyl-4-(2'-pyridylamino)phenyl]propionic acid.

The compounds of the formula (I) can be prepared by reacting a compound of the formula (IV):

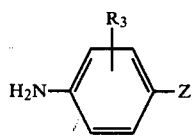 (IV)

wherein $R_3$ is as defined above, Z is

or a group convertible into

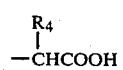

by hydrolysis which is optionally followed by decarboxylation, with a compound of the formula (V):

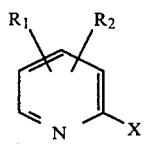 (V)

wherein $R_1$ and $R_2$ are as defined above, X is a halogen (e.g. chlorine or bromine) to give a compound of the formula (I'):

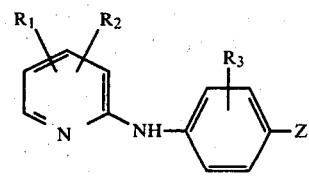 (I')

wherein $R_1$, $R_2$, $R_3$ and Z are as defined above, and optionally hydrolyzing the compound (I') and further optionally subjecting to decarboxylation.

The group convertible into

in the above formula (IV) includes

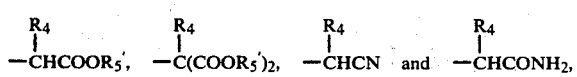

wherein $R_5'$ is an alkyl having 1 to 6 carbon atoms or a phenylalkyl having 1 to 3 carbon atoms in the alkyl moiety. Among these groups, preferred group is

wherein $R_5'$ is an alkyl having 1 to 3 carbon atoms.

The condensation reaction of the compound (IV) and the compound (V) is usually carried out in the absence or presence of a base. A catalyst such as copper powder or cuprous oxide may also be used in the reaction. The reaction may be carried out without using any solvent but may be done in a solvent which does not participate in the reaction, such as toluene, xylene, pyridine, or dimethylformamide. The base used in the reaction includes an alkali metal carbonate (e.g. sodium carbonate or potassium carbonate), an alkali metal bicarbonate (e.g. sodium bicarbonate or potassium bicarbonate), and an organic base (e.g. triethylamine or tri-n-propylamine). The compound (IV) is used in an amount of about 1 to 1.2 mole per 1 mole of the compound (V). The reaction temperature is usually in the range of about 100° to 180° C. and the reaction time is usually from about 30 minutes to about 20 hours.

When the compound (I') wherein Z is a group convertible into

by hydrolysis is obtained in the above reaction, the compound (I') is hydrolyzed by a conventional method to give a compound (I) wherein $R_5$ is hydrogen. For instance, the compound (I') wherein Z is a group convertible into

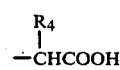

is contacted with water or a water-containing alcohol (e.g. ethanol or isopropanol) at a temperature of room temperature to about 100° C. in the presence of a base (e.g. sodium hydroxide, potassium hydroxide, sodium carbonate, or potassium carbonate) or an acid (e.g. hydrochloric acid, sulfuric acid, or hydrobromic acid). The hydrolysis is generally complete in about 10 minutes to about 5 hours.

When the compound (I') wherein Z is a group convertible into

by hydrolysis and decarboxylation is obtained in the above reaction, the compound (I') is hydrolyzed and then decarboxylated by a conventional method to give a compound (I) wherein $R_5$ is hydrogen. Usually, the compound (I') wherein Z is a group convertible into

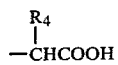

is heated in water or a water-containing alcohol (e.g. ethanol or isopropanol) at about 50° to 100° C. for about 10 minutes to about 8 hours in the presence of about 2 to 3 equivalents of a strong base (e.g. sodium hydroxide or potassium hydroxide), whereby the hydrolysis and decarboxylation proceed simultaneously.

The compound of the formula (I) obtained in the above reaction is isolated and purified in a usual manner.

The racemic mixture of the compound (I) wherein $R_4$ is a lower alkyl and $R_5$ is hydrogen can be resolved with a conventional optically active base (i.e. a resolving reagent) such as cinchonidine or d- or l-α-methylbenzylamine to give each optically active isomer.

The compounds (I) wherein $R_5$ is hydrogen may be converted into a salt thereof with an inorganic or organic base, such as sodium hydroxide, potassium hydroxide, calcium hydroxide, magnesium hydroxide, aluminum hydroxide, ammonium hydroxide, isopropylamine, diethylamine, ethanolamine, piperidine, tromethamine, lysine, or the like. The reaction for converting into a salt may usually be carried out in an appropriate solvent such as water, a lower alcohol (e.g. methanol, ethanol, or isopropanol), toluene, or a mixture thereof at a temperature of about 0° to 100° C. The calcium or magnesium salt of the compound (I) may preferably be obtained by treating the corresponding sodium or potassium salt with calcium chloride or magnesium chloride.

The starting compounds of the formula (V) are commercially available or may be prepared by such a known process as described in E. Elingsberg (ed), "The Chemistry of Heterocyclic Compounds; Pyridine and Its Derivatives Part Two," Interscience Publishers, Inc., New York, 1961, pages 299-383. Besides, the other starting compounds of the formula (IV) are also commercially available or may be prepared by such a known process as described in Experientia, Vol. 29, page 938 (1973).

The pharmacological experimental data of some representative compounds of the present invention are shown below together with the data of a commercially available drug and of some analogous compounds.

The compounds used in the experiments are as follows.

(The compounds of the present invention):
A: 2-[4-(2'-Pyridylamino)phenyl]propionic acid
B: 2-[3-Chloro-4-(2'-pyridylamino)phenyl]propionic acid
(Reference compounds)
1: Ibuprofen which is a well-known anti-inflammatory agent and whose chemical name is 2-(4-isobutylphenyl)propionic acid.
2. 2-[4-[N-Methyl-N-(2'-pyridyl)amino]phenyl]propionic acid which is novel but comes within the general formula given in U.S. Pat. No. 3,766,260.
3: 2-[4-(2'-Pyridyloxy)phenyl]propionic acid disclosed in the specification of Japanese Patent Publication (unexamined) No. 149,668/75.

Ten to 15 animals for each dose of test compounds were used for testing anti-inflammatory and analgesic activities, and 4 to 6 dose levels were used for calculating each $ED_{50}$ (50% effective dose). Six to 15 animals for each dose and 4 to 6 dose levels were used for calculating each $UD_{50}$ (50% ulcer forming dose) or $LD_{50}$ (50% lethal dose).

TEST 1. ANTI-INFLAMMATORY ACTIVITY (EFFECT ON ACUTE INFLAMMATION)

(a) Carrageenin-induced hind paw edema in rats (CAR method)
The test was carried out according to the method described in Proc. Soc. Exp. Biol. Med., 111, 544 (1962).
(b) Acetic acid-induced vascular permeability in mice (CAP method)
The test was carried out according to the method described in Brit. J. Pharm. Chemother., 22, 246 (1964).

TEST 2. ANALGESIC ACTIVITY (a) Phenylquinone-induced writhing in mice (PQW method)
The test was carried out according to the method described in Proc. Soc. Exp. Biol. Med., 95, 729 (1957).
(b) Acetic acid-induced writhing in rats (ACWR method)
The test was carried out according to the method described in Arzneim. Forsch., 25, 1505 (1975).

The results in the above Tests 1 and 2 are shown in Table 1.

TABLE 1

| | Anti-inflammatory and analgesic activities | | | |
|---|---|---|---|---|
| | $ED_{50}$ (mg/kg, p.o.) | | | |
| Test compound | Anti-inflammatory | | Analgesic | |
| | CAR[1] | CAP[2] | PQW[3] | ACWR[4] |
| A | 10.0 | 0.88 | 7.33 | 1.36 |
| B | 13.1 | 3.18 | 8.62 | 1.80 |
| (Reference compound) | | | | |
| 1 | 24.3 | 7.11 | 50.0 | 9.43 |
| 2 | 40.0 | >20.0 | >100 | 20.0 |
| 3 | 20.0 | 6.74 | 80.0 | 5.51 |

[1]CAR: Carrageenin-induced hind paw edema in rats.
[2]CAP: Acetic acid-induced vascular permeability in mice.
[3]PQW: Phenylquinone-induced writhing in mice.
[4]ACWR: Acetic acid-induced writhing in rats.

As is clear from the above results,
(1) the Compounds A and B of the present invention are superior to the known anti-inflammatory agent: ibuprofen (Compound 1) in anti-inflammatory and analgesic activities,
(2) the Compounds A and B are far greater than the known Compound 2 in anti-inflammatory and analgesic activities, and (3) the Compounds A and B are superior in anti-inflammatory activity to and far greater in analgesic activity than the known Compound 3.

TEST 3. EFFECT ON CHRONIC INFLAMMATION MEDIATED BY CELLULAR IMMUNITY

Prophylactic effect of adjuvant-induced arthritis in rats.

The test was carried out according to the method described in Brit. J. Pharmacol., 21, 127 (1963).

Adjuvant (M. tuberculosis $H_{37}Rv$ 0.6 mg/0.06 ml in light mineral oil; Bayol F/rat) was intradermally inoculated into the tail of female rats of JCL:SD strain on day 0. Each compound was administered orally in an amount of 80 mg/kg/day once 3.5 hour before and once a day for 20 days after adjuvant inoculation (0–20 days). The rats of the control group were orally given only vehicle (0.5% gum tragacanth solution).

The results are shown in Table 2 and the accompanying FIGURE. In the FIGURE, the prophylactic effect of the test compounds on adjuvant-induced arthritis in rats is shown by the swelling of hind foot, and the lines (1), (2) and (3) show the data of vehicle control, Compound 1 and Compound A, respectively.

TABLE 2

| Test compound | Dose mg/kg/day p.o. | Arthritic index mean ± S.E. 22nd day | Arthritic index mean ± S.E. 28th day | Arthritic incidence (%) |
|---|---|---|---|---|
| Vehicle control | | 13.1 ± 1.9 | 9.9 ± 1.5 | 100 |
| A (Reference compound) | 80 | 1.3 ± 0.8** | 1.3 ± 0.6** | 0 |
| 1 | 80 | 12.1 ± 2.3 | 10.7 ± 2.3 | 85.7 |

**P < 0.01 significantly different from the vehicle control.

As is clear from the above results, the Compound A of the present invention is far greater than the known ibuprofen (Compound 1) in inhibitory activity against chronic inflammation mediated by cellular immunity. Besides, the compound A shows an anti-allergic activity, but the known ibuprofen does not show such an activity.

TEST 4. GASTROINTESTINAL ULCEROGENICITY

The test was carried out using fasted rats according to the method described in Arzneim. Forch., 19, 36 (1969).

TEST 5. ACUTE LETHAL TOXICITY

The mortality was observed on the 7th day after single oral administration of test compounds in mice, and the $LD_{50}$ was calculated according to the method of Litchfield and Wilcoxon.

The results of the above Tests 4 and 5 are shown in Table 3.

TABLE 3

| Test compound | Ulcerogenicity $UD_{50}$ (mg/kg, p.o.) | Safety index ratio of $UD_{50}/ED_{50}$ (CAR method) | $LD_{50}$ (mg/kg, p.o.) |
|---|---|---|---|
| A (Reference compound) | >640 | >64 | 1907 |
| 1 | 124.6 | 5.1 | 1394 |

As is clear from the above results, the safety index of the Compound A of the present invention is far larger than that of the known ibuprofen and its toxicity is weaker than that of the latter. Besides, it is to be noted that the Compound A has an extremely weak ulcerogenicity in the gastrointestinal tract.

Thus, the compounds of the present invention have an excellent analgesic activity as well as an excellent anti-inflammatory activity with an extremely weak ulcerogenicity in the gastrointestinal tract, and hence, they have a large safety margin. Moreover, they have an excellent inhibitory activity against the chronic inflammation mediated by cellular immunity. Accordingly, the compounds (I) and pharmaceutically acceptable salts thereof are useful as anti-inflammatory and analgesic agents for the treatment of various inflammatory conditions of the muscular skeletal system, skeletal joints and other tissues in mammals including humans, for example, inflammatory conditions such as rheumatism, concussion, laceration, arthritis, bone fractures, post-traumatic conditions, and peritendinitis. When these conditions include pain coupled with inflammation, the compounds of the present invention are useful for the relief of the condition as well as inflammation.

The compounds (I) and pharmaceutically acceptable salts thereof of the present invention can be administered to the patients in oral, parenteral, intrarectal, or topical route.

Dose of the compounds (I) and salts thereof may vary with the kinds of the compounds, the administration routes, the age of the patients, the kinds and severity of the diseases to be treated, or the like, but is in the range of 1 to 60 mg per kg of body weight per day, preferably 2 to 30 mg per kg of body weight per day, for humans. The dose may be divided and administered in two to several times per day.

The compounds (I) and pharmaceutically acceptable salts thereof are usually administered to patients in the form of a pharmaceutical composition which contains a non-toxic and effective amount of the compounds. The pharmaceutical composition is usually prepared by admixing the active compounds (I) or their salts with conventional pharmaceutical carrier materials which are unreactive with the active compounds (I) or their salts. Suitable examples of the carrier materials are lactose, starch, sucrose, microcrystalline cellulose, sodium carboxymethylcellulose, calcium carboxymethylcellulose, methylcellulose, gelatin, acacia, hydroxypropylcellulose, hydroxypropyl methylcellulose, polyvinylpyrrolidone, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerides of saturated fatty acids, anhydrous lanolin, glycerogelatin, macrogol, vegetable oils, wax, cetyl alcohol, oleyl alcohol, propylene glycol, ethanol, isopropanol, water, or the like.

The pharmaceutical composition may be in the dosage form of tablets, capsules, granules, fine granules, powders, syrups, suppositories, ointments, creams, gels, injections, or the like. These preparations may be prepared by conventional methods. Liquid preparations may be prepared by dissolving or suspending the active compounds in water or other suitable vehicles, when used. Tablets may be coated in a conventional manner.

The pharmaceutical composition may contain as the active ingredient the compound (I) or its pharmaceutically acceptable salt in the ratio of 0.5% by weight or more, preferably 3 to 70% by weight, based upon the whole weight of the compositions. The composition may further contain one or more other therapeutically active compounds.

The present invention is illustrated by the following Examples but is not limited thereto. In the Examples, the compound was identified with the elemental analysis, mass spectrum, IR spectrum, NMR spectrum, etc.

EXAMPLE 1

4-(2'-Pyridylamino)phenylacetic acid

A mixture of 3.0 g of p-aminophenylacetic acid, 3.2 g of 2-bromopyridine and 4.3 g of tri-n-propylamine was heated at 170° C. for 3 hours. The reaction mixture was diluted with dilute ammonia, treated with active carbon, and filtered. The filtrate was made acidic with acetic acid and extracted with chloroform. The organic layer was dried over anhydrous sodium sulfate and concentrated. The residue was recrystallized from acetone and then from a mixture of acetone and ethanol to give the title compound (1.5 g, 33%), m.p. 167°–170° C.

EXAMPLE 2

2-[4-(2'-Pyridylamino)phenyl]propionic acid

A mixture of 2.1 g of methyl 2-(4-aminophenyl)propionate and 1.33 g of 2-chloropyridine was heated at 160° C. for 3.5 hours, and then dissolved in 12 ml of methanol. To the solution was added 12 ml of 10% aqueous sodium hydroxide solution and the resulting solution was stirred at room temperature for 30 minutes. After evaporation of the methanol, the solution was adjusted to pH 5 with dilute hydrochloric acid. Crystals precipitated were collected by filtration and recrystallized from methanol to give the title compound (2.0 g, 72%), m.p. 188°–190° C.

EXAMPLE 3

2-(2-Hydroxyethoxy)ethyl 2-[4-(2'-pyridylamino)phenyl]propionate

A mixture of 4.4 g of 2-(2-hydroxyethoxy)ethyl 2-(4-aminophenyl)propionate and 2.75 g of 2-bromopyridine was heated at 160° C. for one hour, and then dissolved in a small amount of methanol. To the solution were added ethyl acetate and dilute aqueous sodium bicarbonate solution. The organic layer was separated, washed, dried over anhydrous sodium sulfate, and concentrated. The residue was chromatographed on silica gel (60 g) using chloroform as an eluent. Fractions containing the title compound were pooled and concentrated to give the title compound (4.3 g, 75%) as an oil.

Analysis-Calcd. for $C_{18}H_{22}N_2O_4$: C, 65.44; H, 6.71; N, 8.48; Found: C, 65.31; H, 6.79; N, 8.22.

Mass Spectrum m/e: 330 (M+)

EXAMPLE 4

Various compounds of the formula:

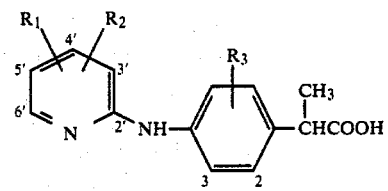

as listed in Table 4 were prepared by reacting the corresponding pyridine compound with the corresponding propionic acid or propionate compound in substantially the same manner as in Examples 1 to 3.

TABLE 4

| $R_1$ | $R_2$ | $R_3$ | Melting point (°C.) | $R_1$ | $R_2$ | $R_3$ | (dl-form) Melting point (°C.) |
|---|---|---|---|---|---|---|---|
| H | H | 3-Cl | 154–156 | 5'-Cl | H | H | 173–175 |
| H | H | 2-Cl | 160–162 | 5'-Br | H | H | 173–175 |
| 3'-CH$_3$ | H | H | 158–160 | 3'-Cl | 5'-Cl | H | 130 |
| 4'-CH$_3$ | H | H | 168–170 | 5'-NO$_2$ | H | H | 170–172 |
| 5'-CH$_3$ | H | H | 165–167 | H | H | 3-CH$_3$ | 193 |
| 6'-CH$_3$ | H | H | 156–158 | | | | |

EXAMPLE 5

Calcium 2-[4-(2'-pyridylamino)phenyl]propionate

2-[4-(2'-Pyridylamino)phenyl]propionic acid (1.21 g) was dissolved in 20 ml of water containing 0.20 g of sodium hydroxide. To the solution cooled in an ice bath was added a solution of 0.368 g of calcium chloride dihydrate in 10 ml of water. The resulting solution was stirred for one hour. After removal of a slight amount of the insoluble materials by filtration, the filtrate was concentrated to a volume of about 10 ml and allowed to cool. Crystals precipitated were collected, washed with water and dried to give the title compound (1.05 g, 74%), m.p. 210°–220° C.

REFERENCE EXAMPLE 1

2-(2-Hydroxyethoxy)ethyl 2-(4-aminophenyl)propionate (The starting material used in Example 3)

(i) A mixture of 5.0 g of 2-(4-nitrophenyl)propionic acid, 20 ml of diethylene glycol and 0.5 ml of concentrated sulfuric acid was heated at 100° C. for one hour, and then poured into ice-water. The resulting mixture was extracted with ethyl acetate. The organic layer was washed with dilute aqueous sodium bicarbonate solution and dried over anhydrous sodium sulfate. After evaporation of the solvent, the residue was chromatographed on silica gel (50 g) using chloroform as an eluent. Fractions containing 2-(2-hydroxyethoxy)ethyl 2-(4-nitrophenyl)propionate were pooled and concentrated.

(ii) The ester compound obtained above was dissolved in 30 ml of ethanol containing 0.1 g of platinum oxide. The solution was hydrogenated until the theoretical amount of hydrogen was absorbed. After removal of the catalyst by filtration, the filtrate was concentrated. The residual oil was chromatographed on silica gel (40 g) using chloroform-methanol (100:1) as an eluent. Fractions containing the title compound were pooled and concentrated to give the title compound (4.6 g, 70%) as an oil.

REFERENCE EXAMPLE 2

2-[4-[N-Methyl-N-(2'-pyridyl)amino]phenyl]propionic acid (Compound 2 used in the pharmacological tests)

A mixture of 5.93 g of 2-bromopyridine and 4.90 g of methyl 2-(4-methylaminophenyl)propionate [prepared by the method described in U.S. Pat. No. 3,957,850] was heated at 160° C. for one hour. The reaction mixture was dissolved in 20 ml of methanol, and 40 ml of 5% aqueous sodium hydroxide solution was added. The solution was stirred at room temperature for 30 minutes, washed with chloroform, adjusted to pH 5 with dilute hydrochloric acid, and extracted with chloroform. The organic layer was dried over anhydrous sodium sulfate and chromatographed on silica gel (100 g) using chloroform-methanol (100:2) as an eluent. Fractions containing the title compound were pooled and concentrated. The residue was recrystallized from diethyl ether to give the title compound (3.60 g, 55%), m.p. 120°–121° C.

EXAMPLE 6

| | |
|---|---|
| 2-[4-(2'-Pyridylamino)phenyl]propionic acid | 50 g |
| Corn starch | 18 g |
| Lactose | 40 g |
| Microcrystalline cellulose | 80 g |
| Hydroxypropylcellulose | 10 g |
| Light anhydrous silicic acid | 1 g |
| Magnesium stearate | 1 g |

The above components were blended, granulated and made into tablets by a conventional method to form 1,000 tablets each weighing 200 mg.

EXAMPLE 7

| | |
|---|---|
| 2-[4-(2'-Pyridylamino)phenyl]propionic acid | 100 g |
| Corn starch | 66 g |
| Lactose | 50 g |
| Microcrystalline cellulose | 30 g |
| Talc | 2 g |
| Magnesium stearate | 2 |

The above components were blended, granulated and filled into 1,000 capsules by a conventional method.

EXAMPLE 8

| | per 1000 suppositories |
|---|---|
| 2-[4-(2'-Pyridylamino)phenyl]propionic acid | 150 g |
| Witepsol W35 (glycerides of saturated fatty acids, a product of Dynamit Nobel Chemicals) | 1,350 g |

The above components were made into 1,000 suppositories each weighing 1,500 mg by a conventional method.

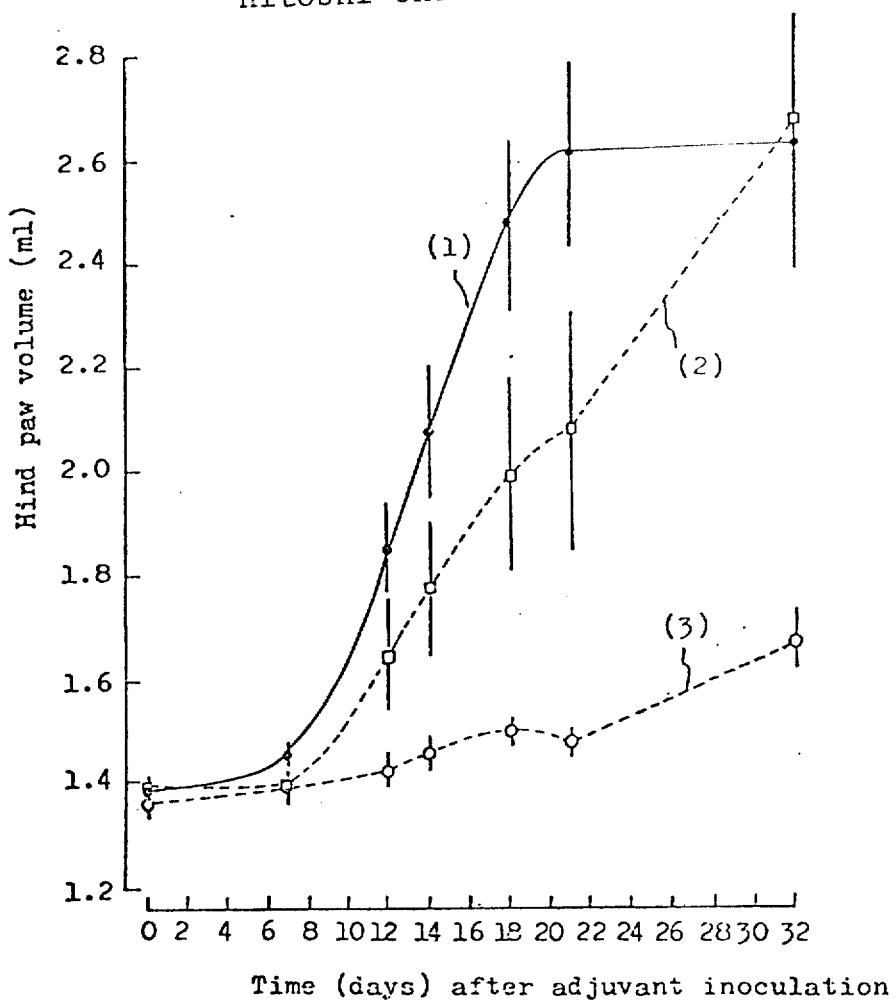

What is claimed is:

1. A compound of the formula:

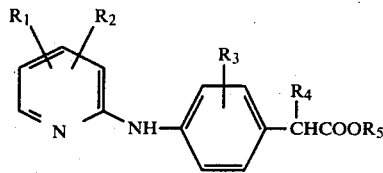

wherein $R_1$ is hydrogen, a halogen, a lower alkyl having 1 to 3 carbon atoms, or nitro, $R_2$ is hydrogen, a halogen, or a lower alkyl having 1 to 3 carbon atoms, $R_3$ is hydrogen, a halogen, or a lower alkyl having 1 to 3 carbon atoms, $R_4$ is hydrogen or a lower alkyl having 1 to 3 carbon atoms, $R_5$ is hydrogen or $-CH_2CH_2OR_6$ wherein $R_6$ is a lower alkyl having 2 or 3 carbon atoms and being substituted with 1 or 2 hydroxy groups, provided that $R_1$ or $R_2$ is not 4-halogen, or a pharmaceutically acceptable salt thereof.

2. A compound according to claim 1, wherein $R_1$ is hydrogen, a halogen or nitro and $R_2$ is hydrogen or a halogen, or a pharmaceutically acceptable salt thereof.

3. A compound of the formula:

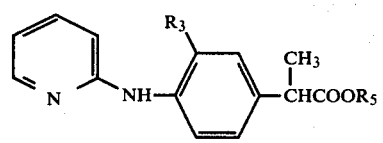

wherein $R_3$ is hydrogen, a halogen or methyl and $R_5$ is hydrogen or 2-(2-hydroxyethoxy)ethyl, or a pharmaceutically acceptable salt thereof.

4. 2-[4-(2'-Pyridylamino)phenyl]propionic acid or a pharmaceutically acceptable salt thereof.

5. 2-[3-Chloro-4-(2'-pyridylamino)phenyl]propionic acid or a pharmaceutically acceptable salt thereof.

6. 2-[3-Methyl-4-(2'-pyridylamino)phenyl]propionic acid or a pharmaceutically acceptable salt thereof.

7. An anti-inflammatory and analgesic pharmaceutical composition for the treatment of body tissues of mammals and humans comprising an effective amount of a compound of the formula:

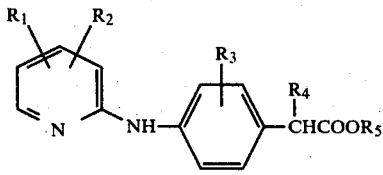

wherein $R_1$ is hydrogen, a halogen, a lower alkyl having 1 to 3 carbon atoms, or nitro, $R_2$ is hydrogen, a halogen, or a lower alkyl having 1 to 3 carbon atoms, $R_3$ is hydrogen, a halogen, or a lower alkyl having 1 to 3 carbon atoms, $R_4$ is hydrogen or a lower alkyl having 1 to 3 carbon atoms, $R_5$ is hydrogen or $-CH_2CH_2OR_6$ wherein $R_6$ is a lower alkyl having 2 or 3 carbon atoms and being substituted with 1 or 2 hydroxy groups, provided that $R_1$ or $R_2$ is not 4-halogen, or a pharmaceutically acceptable salt thereof and a pharmaceutically acceptable carrier.

8. A pharmaceutical composition according to claim 7, wherein said compound is 2-[4-(2'-pyridylamino)-phenyl]propionic acid or a pharmaceutically acceptable salt thereof.

9. The method of treating mammals and humans with the pharmaceutical composition of claim 7.

* * * * *

UNITED STATES PATENT AND TRADEMARK OFFICE
CERTIFICATE OF CORRECTION

PATENT NO. : 4,256,753
DATED : March 17, 1981
INVENTOR(S) : Hitoshi Uno et al.

It is certified that error appears in the above—identified patent and that said Letters Patent is hereby corrected as shown below:

On The Title Page, delete "No Drawings" and insert

-- 1 Drawing Figure --. (See attached sheet)

Column 11, line 49, "2" should read -- 2g --.

Signed and Sealed this

Twenty-second Day of September 1981

[SEAL]

Attest:

GERALD J. MOSSINGHOFF

Attesting Officer    Commissioner of Patents and Trademarks